(12) United States Patent
Lee et al.

(10) Patent No.: US 7,772,418 B1
(45) Date of Patent: Aug. 10, 2010

(54) PROCESS FOR PRODUCING 3,4' DIACETOXYBENZOPHENONE

(75) Inventors: Kiu-Seung Lee, Midlothian, VA (US); Michael Francis Vincent, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/393,295

(22) Filed: Feb. 26, 2009

(51) Int. Cl.
*C07C 69/00* (2006.01)

(52) U.S. Cl. .................................. 560/130; 560/138

(58) Field of Classification Search .................. 560/130, 560/138
See application file for complete search history.

(56) References Cited

U.S. PATENT DOCUMENTS

| 4,245,082 A | 1/1981 | Irwin |
| 4,269,965 A | 5/1981 | Irwin |
| 4,500,699 A | 2/1985 | Irwin et al. |
| 4,617,369 A * | 10/1986 | Huynh-Ba .................. 528/128 |

\* cited by examiner

*Primary Examiner*—Sikarl A Witherspoon

(57) ABSTRACT

A process for producing 3,4'diacetoxybenzophenone by first synthesizing 3,4'dihydroxybenzophenone by reacting meta-hydroxybenzoic acid and phenol in the presence of a Lewis acid, and a protonic acid followed by reacting the 3,4'dihydroxybenzophenone with an acetylating agent in the presence of an inorganic acid and activated carbon.

12 Claims, No Drawings

PROCESS FOR PRODUCING 3,4' DIACETOXYBENZOPHENONE

BACKGROUND OF INVENTION

1. Field of Invention

This invention is directed to a process for producing 3,4' diacetoxybenzophenone.

2. Description of the Related Art

Various processes are disclosed in the art for producing 3,4' diacetoxybenzophenone (also known as 3,4' dihydroxybenzophenone diacetate) including U.S. Pat. No. 4,269,965 issued May 26, 1981, U.S. Pat. No. 4,245,082 issued Jan. 13, 1981, and U.S. Pat. No. 4,500,699 issued Feb. 19, 1985 all to Robert S. Irwin.

There is a need for an improved, efficient, and economical process for producing 3,4' diacetoxybenzophenone.

SUMMARY OF THE INVENTION

The present invention is directed a method for producing 3, 4' diacetoxybenzophenone comprising in order:
- (a) combining m-hydroxybenzoic acid, phenol, a protonic acid and a Lewis acid to form a mixture,
- (b) heating an agitated mixture of step (a) to a temperature in a range of 27-33° C. and a pressure of at least 5 psig to form a reaction product of 3,4' dihydroxybenzophenone present as solids in a solution,
- (c) removing at least a portion of the protonic acid and Lewis acid from the formed reaction product of 3,4' dihydroxybenzophenone,
- (d) contacting the reaction product of step (c) with (i) water at a temperature not greater than 10° C. and (ii) ammonium hydroxide to obtain a pH in a range of 4.5 to 6;
- (e) filtering a mixture of step (d) to separate 3,4' dihydroxybenzophenone solids
- (f) reacting 3,4' dihydroxybenzophenone with an acetylating agent in the presence of an inorganic acid and activated carbon to form 3,4' diacetoxybenzophenone.

Preferably purified 3,4' diacetoxybenzophenone is obtained by:
- (g) filtering 3,4' diacetoxybenzophenone of step (f) through an acid pre-washed diatomaceous earth filter to produce a filtrate;
- (h) contacting the 3,4' diacetoxybenzophenone filtrate with water at a temperature not greater than 10° C. and;
- (i) separating the water from the 3,4' diacetoxybenzophenone.

DETAILED DESCRIPTION OF THE INVENTION

Synthesis of 3,4' dihydroxybenzophenone

An initial first step in formation of 3,4 dihydroxybenzophenone is to form a mixture of m-hydroxybenzoic acid, phenol, a protonic acid and a Lewis acid. (As employed herein formation of a "mixture" may include formation of a "solution".)

Preferably the m-hydroxybenzoic acid and phenol are present in equimolar amounts to form the 3,4' dihydroxybenzophenone. It is understood that either the m-hydroxybenzoic acid or phenol may be present in excess compared to the exact ratio needed. However in such case the excess reactant will be present as an impurity in the formed 3,4' dihydroxybenzophenone.

For purposes of explanation, equimolar amounts means that reactants are combined such that the same number of moles of reactants are combined together. Another way of expressing this is that a ratio of the number of moles of reacted meta-hydroxybenzoic acid divided by the number of moles of reacted phenol is equal to one.

Protonic acids, as employed herein, are acids that form positive hydrogen ions or oxonium ($H_3O^+$) ions in an aqueous solution. Suitable protonic acids include hydrofluoric acid (hydrogen fluoride), hydrochloric acid, sulphuric acid, and hydrobromic acid (hydrogen bromide). It is understood that mixtures of the acids can be used. A preferred protonic acid is hydrofluoric acid (hydrogen fluoride).

Examples of Lewis acids useful include aluminum chloride, iron(III) chloride, boron trifluoride, niobium pentachloride and lanthanide triflates such as ytterbium(III) triflate. Mixtures of the acid can also be employed. A preferred Lewis acid is boron trifluoride.

Preferably formation of a mixture of m-hydroxybenzoic acid, phenol, a protonic acid and a Lewis acid is undertaken in several segments. A first segment involves forming a solution of meta-hydroxybenzoic acid, phenol and a protonic acid. As previously set forth a preferred protonic acid is hydrofluoric acid. Preferably the protonic acid is present in an amount of a least two times the total weight of the meta-hydroxbenzoic acid and phenol.

In the preferred mode, a second segment involves a separate addition of the Lewis acid to the solution of meta-hydroxybenzoic acid, phenol and protonic acid. As previously set forth a preferred Lewis acid is boron trifluoride.

Typically the mixture of m-hydroxybenzoic acid, phenol, a protonic acid and a Lewis acid is present in a pressure vessel, commonly known as a pressure reactor. The mixture in the reactor is heated to a temperature in a range of 27 to 33° C. and the pressure is allowed to increase to at least 5 psig thereby forming a reaction product of 3,4' dihydroxybenzophenone. Preferably the contents of the pressure reactor are agitated during the reaction.

For purposes of illustration a time of heating employing elevated pressure is a minimum of 4 hours. Also preferably, the reaction mixture is allowed to return to room temperature over a prolonged time period such as 16 hours.

After release of the elevated pressure in the reactor, protonic acid and the Lewis acid are removed from the reaction mixture. A conventional separation method such as rotary distillation is suitable employing reduced temperature and pressure.

The reaction mixture then is contacted with water at a temperature not greater than 10° C. to extract residual protonic and Lewis acids, water soluble reactants and water soluble byproducts from the reaction mixture followed by use of aqueous ammonium hydroxide to neutralize remaining residual acid and to elevate the pH of the reaction mixture to a range of 4.5 to 6.

The resulting reaction mixture present as an aqueous slurry is then filtered to recover 3,4' dihydroxybenzophenone as a salmon colored solid. The resulting 3,4' dihydroxybenzophenone preferably is washed with water and with cold methanol at a temperature of less than 15° C. to remove any residual water soluble impurities.

Typically, the resulting 3,4'dihydroxybenzophenone is present in a yield based on weight of at least 70%, preferably 80%, and most preferably at least 87% based on equimolar quantities of meta-hydroxybenzoic acid and phenol. The final product of this synthesis and can be used without further purification. Optionally, the resulting 3, 4' dihydroxybenzophenone can be dried before further use. The melting point for this product was found to be in the range of 200-201° C.

Synthesis of 3,4' diacetoxybenzophenone (3,4' dihydroxybenzophenone diacetate)

3, 4' diacetoxybenzophenone (3,4' dihydroxybenzophenone diacetate) is made by reacting 3,4' dihydroxybenzophenone with an acetylating agent in the presence of an inorganic acid and activated carbon.

The acetylating agent is acetic anhydride, as a precursor, or acetic acid. Acetic anhydride when contacted with water readily hydrolyzes to yield acetic acid. Because of acetic anhydride's tendency to rapidly hydrolyze, mixtures of acetic anhydride and acetic acid in any proportion can also be used as an acetylating agent.

Inorganic acids useful in this synthesis include sulfuric acid, hydrochloric acid, phosphoric acid, hydrofluoric acid (hydrogen fluoride), and hydrobromic acid (hydrogen bromide) and mixtures thereof.

Concentrated sulfuric acid is suitable at a concentration of at least 90% sulfuric acid by weight. Illustratively the amount of acid is in a range from 500 to 2000 ppm based on the weight of 3,4' dihydroxybenzophenone. A narrower range is 750-1000 ppm.

Activated carbon, as defined herein, has a carbon content of 80-94% by weight, and a surface area of 500 to 1500 $m^2$/gram (square meter/gram). Illustratively the amount of activated carbon is in a range from 0.1 to 10% by weight of the reactants of 3,4' dihydroxybenzophenone and acetic anhydride. A narrower range of activated carbon is 5 to 7 weight percent. Commercially available grades of activated carbon include Darco® 12X12, Darco® G-60, and Darco® KB-WJ supplied by Norit Americas, Mashall, Tex.

Treatment of the diatomaceous earth filter can be completed with acetic anhydride, acetic acid and any mixtures thereof.

In a preferred embodiment the 3, 4' diacetoxybenzophenone is filtered through diatomaceous earth filter to produce a filtrate. Diatomaceous earth is a naturally occurring siliceous sedimentary mineral compound composed of the microscopic skeletal remains of unicellular algae-like plants called diatoms. The general composition of diatomaceous earth is approximately 3% magnesium, 33% silicon, 19% calcium, 5% sodium, 2% iron and other trace minerals such as titanium, boron, manganese, copper and zirconium by weight. Diatomaceous earth is commonly sold under the trade name as Celite®. Optionally the diatomaceous earth is first pre-washed with acetic acid prior to use.

Also, in a preferred embodiment the 3, 4' diacetoxybenzophenone filtrate is contacted with a solution of ice and water at a temperature not greater than 10° C. followed by filtering to separate water form the 3, 4' diacetoxybenzophenone.

Further optional steps include washing the 3,4'diacetoxybenzophenone with deionized water followed by drying.

3,4' diacetoxybenzophenone is useful in manufacture of LCP (liquid crystal polyester) polymers. Illustratively, terephthalic acid can be reacted with 3,4' diacetoxybenzophenone to produce a liquid crystal polyester.

In the following examples, all parts and percentages are by weight and all temperatures are in degrees Celsius unless otherwise stated.

Example 1

Preparation of 3,4'-dihydroxybenzophenone

A pressure reactor was charged with 44 g of m-hydroxybenzoic acid, 32 g of phenol and 200 g of anhydrous hydrogen fluoride. The vessel was charged with 36.7 g of boron trifluoride gas and heated to 30° C. for four hours. The reaction mixture was then continuously rocked overnight at ambient temperature. The pressure was bled off and excess hydrogen fluoride was distilled into a caustic scrubber. The vessel was opened and the contents poured into 1 liter of ice water. An aqueous ammonium hydroxide solution (28.0-30.0% $NH_3$ basis by weight) was added to neutralize the batch to a pH of 4.5-6 and the slurry was filtered and the cake was washed 3 times with water and once with ice-cold methanol. The wet filter cake was recovered and dried overnight in a vacuum oven at 80° C. A resulting hard, lumpy material was ground to give 51.5 g of 3,4'-dihydroxybenzophenone, as a salmon colored powder with mp of 200-201° C. Residual product in the methanol filtrate was concentrated and cooled in an ice bath to give a second crop of product. The material was dried in an oven and ground to give 8.5 g of a beige powder. The two crops were identical by NMR and combined to give 60.0 g (87.9%)/0 yield) of intermediate for use in Example 2.

Example 2

Preparation of 3,4'-diacetoxybenzophenone 562.5 g of 3,4'-dihydroxybenzophenone of Example 1, was added to 1700 g of acetic anhydride containing 6 drops of concentrated sulfuric acid and 150 g of Darco® activated carbon. This reaction mixture was then refluxed for 3 hours. The reaction mixture was cooled to room temperature, stirred overnight and filtered through a Celite® bed that was pre-washed with acetic acid. A 20 liter jacketed reactor equipped with a mechanical stirrer was charged with 6.0 liters of ice water and cooled to about 0° C. The acetic anhydride filtrate was added via addition funnel into the ice water over a period of about 2.0 hours with continuous stirring. The slurry was filtered cold, washed four times with deionized water and partially dried on the filter. The product was then dried for about 48 hours in a vacuum oven at 60° C. to give 649.5 g (82.9% yield) of 3,4'diacetoxybenzophenone as a slightly, off-white solid with mp (melting point) of 83.0-84.5° C. $^1$H NMR was consistent with 3,4'diacetoxybenzophenone having a purity of >99.5%.

Comparative Example 1

Preparation of 3,4'-dihydroxybenzophenone

A pressure reactor was charged with 44 g of m-hydroxybenzoic acid, 32 g of phenol and 200 g of anhydrous hydrogen fluoride. The vessel was pressured with boron trifluoride gas and heated to 30° C. for four hours. The pressure was bled off and the excess HF was distilled to a caustic scrubber. The vessel was opened and the contents were poured into aqueous $NaHCO_3$ solution. The slurry (about 2 gallons) was filtered and the cake was washed with water, 5% aqueous $NaHCO_3$ solution and finally with water for a second time. The wet filter cake was dried for about 2 days in a vacuum oven at 80° C. This resulted in 41.4 g of 3,4'-dihydroxybenzophenone (60.6% yield).

What is claimed is:

1. A method for producing 3, 4' diacetoxybenzophenone comprising in order:
   (a) combining m-hydroxybenzoic acid, phenol, a protonic acid and a Lewis acid to form a mixture,
   (b) heating an agitated mixture of step (a) to a temperature in a range of 27-33° C. and a pressure of at least 5 psig to form a reaction product of 3,4' dihydroxybenzophenone present as solids in a solution, (c) removing at least a portion of the protonic acid and Lewis acid from the formed reaction product of 3,4' dihydroxybenzophenone, (d) contacting the reaction product of step (c) with (i) water at a temperature not greater than 10° C. and (ii) ammonium hydroxide to obtain a pH in a range of 4.5 to 6;

(e) filtering a mixture of step (d) to separate 3,4' dihydroxybenzophenone solids (f) reacting 3,4' dihydroxybenzophenone with an acetylating agent in the presence of an inorganic acid and activated carbon to form 3,4' diacetoxybenzophenone.

2. The method of claim 1 wherein step (a) comprises (i) forming a solution of meta-hydrobenzoic acid, phenol and protonic acid, (ii) adding Lewis acid to the solution of step (i).

3. The method of claim 1 wherein the protonic acid is hydrogen fluoride, sulfuric acid or hydrobromic acid.

4. The method of claim 3 wherein the protonic acid is hydrogen fluoride.

5. The method of claim 1 wherein the weight of protonic acid is at least two times the total weight of meta-hydrobenzoic acid and phenol.

6. The method of claim 1 wherein the Lewis acid is aluminum chloride, iron(III) chloride, boron trifluoride, niobium pentachloride or lanthanide frigate.

7. The method of claim 6 wherein the Lewis acid is boron trifluoride.

8. The method of claim 1 wherein the protonic acid is hydrogen flouride and the Lewis acid is boron triflouride.

9. The method according to claim 1 where the pressure of step (b) is at least 10 psig.

10. The method of claim 1 wherein the inorganic acid is sulfuric acid, hydrochloric acid, phosphoric acid, hydrofluoric acid or hydrobromic acid.

11. The method of claim 1 with an added step of:

(g) filtering 3,4' diacetoxybenzophenone of step (f) through an acid pre-washed diatomaceous earth filter to produce a filtrate.

12. The method of claim 11 with the added steps of:

(h) contacting the 3,4' diacetoxybenzophenone filtrate with water at a temperature not greater than 10° C. and;

(i) separating the water from the 3,4' diacetoxybenzophenone.

* * * * *